United States Patent [19]
Schnall et al.

[11] Patent Number: 5,476,095
[45] Date of Patent: Dec. 19, 1995

[54] INTRACAVITY PROBE AND INTERFACE DEVICE FOR MRI IMAGING AND SPECTROSCOPY

[75] Inventors: Mitchell D. Schnall, Lansdowne; Robert E. Lenkinski, Drexel Hill; Herbert Y. Kressel, Wynnewood; Howard M. Pollack, Cheltenham, all of Pa.

[73] Assignees: Medrad, Inc.; University of Pennsylvania, both of Pittsburgh, Pa.

[21] Appl. No.: 203,245

[22] Filed: Mar. 1, 1994

Related U.S. Application Data

[62] Division of Ser. No. 949,918, Sep. 24, 1992, Pat. No. 5,348,010, which is a division of Ser. No. 875,216, Apr. 28, 1992, abandoned, which is a continuation of Ser. No. 315,749, Feb. 27, 1989, abandoned, and a continuation-in-part of Ser. No. 884,470, May 14, 1992, abandoned, which is a continuation of Ser. No. 314,809, Feb. 24, 1989, abandoned.

[51] Int. Cl.$^6$ ..................................................... A61B 5/055
[52] U.S. Cl. ......................................... 128/653.2; 128/653.5
[58] Field of Search ............................... 128/653.2, 653.5, 128/656–658, 772; 604/96–101, 104, 117

[56] References Cited

U.S. PATENT DOCUMENTS

| | | | |
|---|---|---|---|
| 2,085,644 | 6/1937 | Ferciot | 128/788 |
| 2,126,257 | 8/1938 | Hird | 128/788 |
| 4,338,942 | 4/1982 | Fogarty et al. | |

(List continued on next page.)

FOREIGN PATENT DOCUMENTS 0214721   3/1987   European Pat. Off. .

OTHER PUBLICATIONS

J. F. Schenck et al., "High Resolution Magnetic Resonance Imaging Using Surface Coils," Resonance Annual, p. 123 (1986).

Schnall et al., "The Development of an Intracavitary Inflatable Surface Coil for High Resolution Proton Imaging and Spectroscopy," Society of Magnetic Resonance in Medicine (Aug. 1986).

J. F. Martin et al., "Inflatable Surface Coil for MR Imaging of the Prostate", (Apr. 1988).

R. J. Otto et al., "High Resolution MR Imaging of the Prostate" Society of Magnetic Resonance Imaging, (Feb. 1987).

*Primary Examiner*—Ruth S. Smith
*Attorney, Agent, or Firm*—Keck, Mahin & Cate

[57] ABSTRACT

An insertable pickup probe and interface network for magnetic resonance imaging and spectroscopy. The pickup probe in the preferred embodiment is for use in imaging the male prostate and comprises an elongated shaft supporting a patient interface balloon at its distal end which contains a RF receiving coil. The interface balloon comprises an inflatable inner balloon enclosed by a flexible outer balloon. The receiving coil is positioned between the inner and outer balloons and placed intimately adjacent the region of interest by inflating the inner balloon to expand outwardly against the outer balloon. In addition, a non-stretchable planar material is provided on the surface on the inner balloon adjacent the receiving coil for ensuring that the receiving coil is placed adjacent the region of interest. The inner balloon is inflated by an inflator cuff connected to the shaft and communicated to the inner balloon by a first lumen in the shaft. The receiving coil is electrically connected to an interconnecting cable which is connected to the proximal end of the shaft and communicated to the receiving coil by a second lumen in the shaft. The interface network receives the interconnecting cable of the pickup probe and includes impedance matching means, tuning means, and decoupling means for interfacing the probe with a magnetic resonance imaging scanner. In addition, the interface includes an electronic circuit for automatically adjusting the control voltage of a varactor diode in a Pi network which comprises the tuning means.

29 Claims, 6 Drawing Sheets

U.S. PATENT DOCUMENTS

| | | |
|---|---|---|
| 4,398,149 | 8/1983 | Zens . |
| 4,545,390 | 10/1985 | Leary . |
| 4,587,493 | 5/1986 | Sepponen . |
| 4,617,936 | 10/1986 | Malko . |
| 4,620,155 | 10/1986 | Edelstein . |
| 4,636,730 | 1/1987 | Bottomley . |
| 4,646,024 | 2/1987 | Schenck et al. . |
| 4,649,348 | 3/1987 | Flugan . |
| 4,672,972 | 6/1987 | Berke ............................ 128/653.5 |
| 4,680,549 | 7/1987 | Tanttu . |
| 4,692,705 | 9/1987 | Hayes . |
| 4,775,371 | 10/1988 | Mueller, Jr. . |
| 4,793,351 | 12/1988 | Landman et al. . |
| 4,911,163 | 3/1990 | Fina ................................ 606/127 |
| 4,920,318 | 4/1990 | Misic et al. ..................... 128/653.2 |
| 4,932,411 | 6/1990 | Fritschy et al. ................. 128/653.5 |
| 4,960,106 | 10/1990 | Kubukawa et al. ............. 128/6535 C |
| 4,989,608 | 2/1991 | Ratner ............................ 128/653 A |
| 5,035,231 | 7/1991 | Kubokawa et al. ............. 128/653.5 |
| 5,050,607 | 9/1991 | Bradley et al. ................. 128/653.2 |
| 5,071,406 | 12/1991 | Jang . |
| 5,108,370 | 12/1991 | Walinsky . |
| 5,170,789 | 12/1992 | Narayan et al. ................ 128/653.5 |

FOREIGN PATENT DOCUMENTS

| | | |
|---|---|---|
| 0249338 | 12/1987 | European Pat. Off. . |
| 61-90525 | 5/1986 | Japan . |
| 62-286451 | 12/1987 | Japan . |
| 63-49150 | 3/1988 | Japan . |
| 63-270036 | 11/1988 | Japan . |
| 64-20832 | 1/1989 | Japan . |
| 84/01513 | 4/1984 | WIPO . |
| 88/00071 | 1/1988 | WIPO . |

INTRACAVITY PROBE AND INTERFACE DEVICE FOR MRI IMAGING AND SPECTROSCOPY

This application is a divisional of U.S. patent application Ser. No. 07/949,918, filed Sep. 24, 1992, now U.S. Pat. No. 5,348,010 which is a divisional of U.S. patent application Ser. No. 07/875,216, filed Apr. 28, 1992, now abandoned which is a continuation of U.S. patent application Ser. No. 07/315,749, filed Feb. 27, 1989, now abandoned, and this is also a continuation-in-part of U.S. patent application Ser. No. 07/884,470, filed May 14, 1992, which is a continuation of U.S. patent application Ser. No. 07/314,809, filed Feb. 24, 1989, now abandoned.

BACKGROUND OF THE INVENTION

The present invention relates to a receiving device for use in magnetic resonance imaging (MRI) and spectroscopy systems to enhance the imaging performance and spectroscopy sensitivity of such instruments when evaluating anatomical regions small in size relative to the body, and deep within the body, but proximate a location where an insertable pickup probe could be used. Specifically, the present invention relates to an intracavity pickup probe designed to image the prostate region by rectal introduction, to image the cervix region by vaginal introduction, or the like.

In the field of MRI systems, also commonly known as NMR imaging systems, external pickup probes are typically used for receiving radio frequency signals from the region of interest. For optimum performance however, the pickup probe should be insertable for intracavity use and which includes a radio frequency receiving coil, to be positioned as close to the region of interest as possible. In addition, the insertable pickup probe should also have a sensitive volume equaling the desired field of view of the region of interest. This allows optimization of the "filling factor" and "coupling coefficient" for the specific MRI system, thereby improving signal to noise ratio in MR imaging.

Furthermore, for optimum sensitivity, the receiving coil should have an unloaded coil quality factor (Q) which is as great as possible and should be adjusted to resonate at the exact Larmour frequency of the scanner of the MRI system. It also sometimes is desired that the insertable, intracavity pickup probe be disposable, and hence the cost of the probe should be minimized as much as possible. At the same time, it is important that in reducing the cost of the probe, the ability to impedance match and tune the receiving coil to the scanner of the MRI system not be compromised. Therefore, there is a need to provide a disposable pickup probe at minimal cost for use in a MRI system which is capable of automatically or manually tuning and impedance matching the receiving coil to the scanner of the MRI system.

SUMMARY OF THE INVENTION

It is a primary object of the present invention to provide an insertable MRI pickup probe and an interface network having the ability to match the coil of the pickup probe to the resonant frequency of an MRI scanner in an MRI system.

It is an additional object of the present invention to provide an insertable, intracavity pickup probe capable of being placed in close proximity to the region of interest to improve the quality of a magnetic resonance image or spectrum.

It is a further object of the present invention to provide an insertable MRI pickup probe and an interface system having the ability to perform resonant frequency adjustments from a remote location after the probe is inserted into the body of a patient.

It is yet another object of the present invention to provide an insertable MRI pickup probe having a receiving coil, and an interface network having the ability to automatically match the output impedance of the receiving coil with the input impedance of an MRI scanner after the probe is inserted into the body of the patient.

The present invention in its most specific embodiment relates to an insertable, intracavity pickup probe, and more specifically an intrarectal pickup probe and an associated interface network for high sensitivity and high resolution imaging of the male prostate gland and associated area. Although the pickup probe is described hereinafter as principally to image or obtain spectra from the area of the male prostate gland, it should be understood that the concepts outlined herein are equally appropriate for other regions of interest such as the rectum, vagina, and mouth. Additionally, the principles described herein may be applied to MRI or NMR applications involving the arteries, veins, and other similar regions of the body reachable by an insertable or implantable pickup probe.

The insertable pickup probe of the present invention greatly improves the signal-to-noise ratio of an image or spectrum acquisition over signal pickup devices commonly used with MRI and NMR scanner systems. In addition, the restricted field of view of the probe reduces or eliminates image distortion caused by motion, blood flow, patient breathing, and signal aliasing when conducting an image acquisition using multidimensional fast Fourier transform techniques.

The insertable pickup probe of the present invention comprises a shaft which supports an inflatable patient interface balloon at its distal end. In a specific embodiment, the interface balloon comprises an inner balloon and an outer balloon, between which a receiving coil is positioned. A lumen for air supply is provided in the shaft for expanding the inner balloon outwardly against the outer balloon to place the receiving coil in close proximity to the region of interest once the insertable pickup probe is inserted into the body of the patient. In the specific embodiment of the present invention, the pickup probe is a prostate probe and is designed for insertion into the body intrarectally. An anti-migration disc is provided which fits onto the shaft of the probe to prevent migration of the probe superiorly during the normal peristaltic activity of the colon. Furthermore, an introducer is provided which surrounds the shaft and slides over the entire length of the shaft. The introducer functions as a dilator for the anal sphincter during insertion.

The insertable pickup probe of the present invention allows for accurate longitudinal and radial positioning of the balloon within the body by making the shaft rigid when twisted radially, the balloon, shaft and handle are bonded together so that they move radially as a single unit when torque is applied. The distal tip of the probe is more flexible than the shaft to avoid perforating tissue during use.

An inflater cuff is provided which connects to the shaft and functions as an air pump to deliver a volume-limited amount of air through the air lumen of the shaft to the inner balloon. Furthermore, a stop cock is provided to maintain the air within the inner balloon. The receiving coil extends through another lumen of the shaft and connects to an interconnecting cable which electrically connects the receiving coil to the interface network. Typically, the probe, with built-in balloon, receiving coil, inflator cuff and including the shaft, anti-migration disc, and introducer, is disposable.

The interface network of the present invention performs three functions in conjunction with the insertable pickup probe and a MRI or NMR scanner of an imaging system. First, the interface network tunes the receiving coil of the pickup probe to the Larmour frequency of the scanner. Second, the interface network matches the output impedance of the probe to the input impedance of the scanner. Third, the interface network decouples the receiving coil during the transmitting portion of a scanning sequence, if the probe is used as a receive only coil.

Tuning of the receiving coil to the Larmour frequency of the MRI scanner is accomplished manually or automatically. In the preferred embodiment, the interface network is an electronic optimization circuit to automatically adjust the resonance frequency seen at the output of the probe. In addition, in alternative versions, the interface network includes an electronic optimization circuit to allow automatic optimization of both the tuning and the impedance transformation ratio.

The above and other objects and advantages of the present invention will become more readily apparent when reference is made to the following description, taken in conjunction with the accompanying drawings.

DETAILED DESCRIPTION OF THE DRAWINGS

Figure 1:
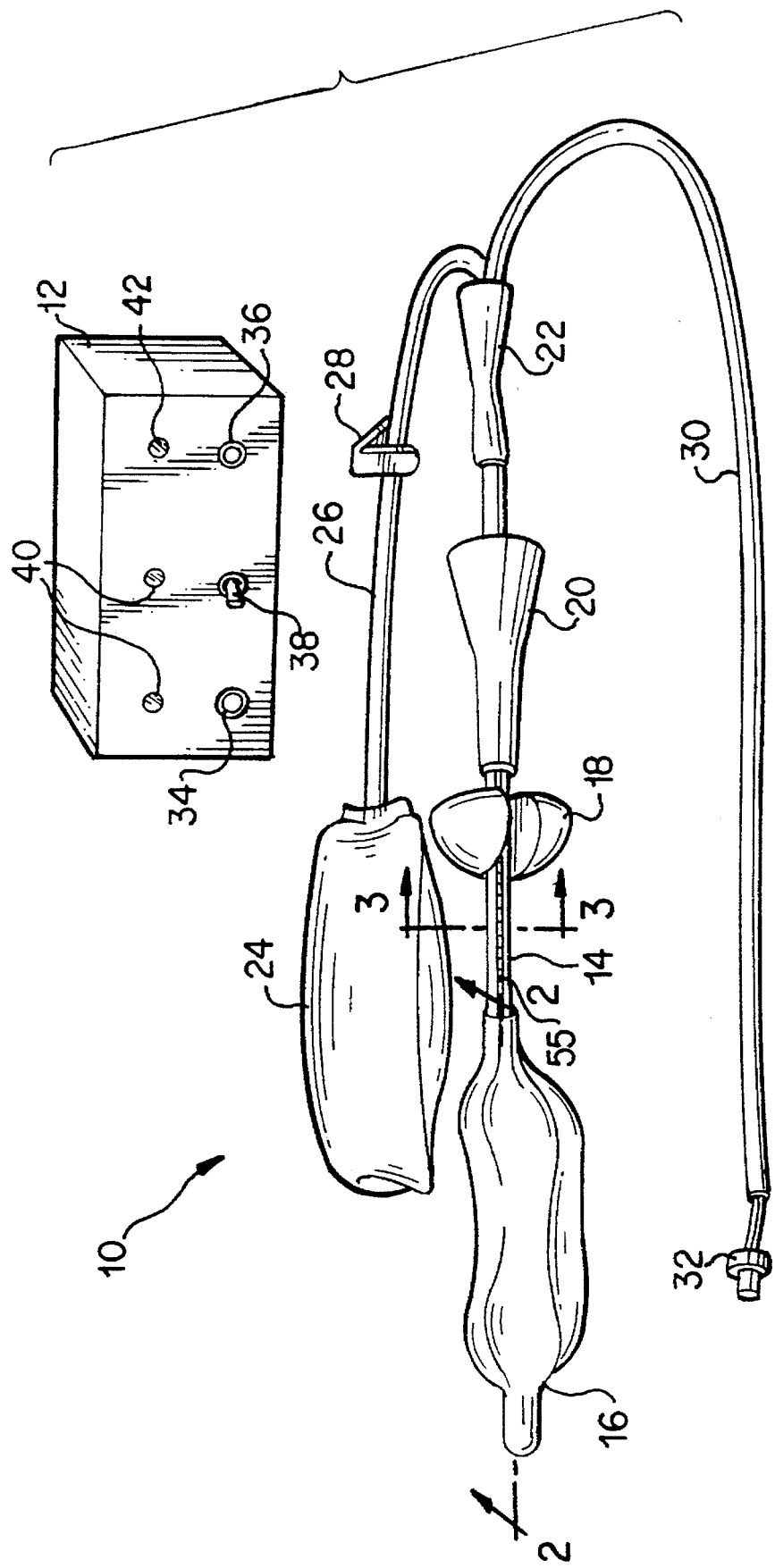
FIG. 1 is a perspective view illustrating the insertable pickup probe and the interface network in accordance with the present invention.

Referring first to FIG. 1, the insertable prostate pickup probe is shown in an assembled form at 10, which connects to an interface network 12. The insertable prostate pickup probe 10 is an MRI or NMR receiving device capable of imaging or gathering spectra from the human prostate and surrounding tissue, but may also be used as the transmit coil for RF excitation. The probe 10 is used with the interface network 12 which provides the tuning, impedance matching, and decoupling functions.

The probe 10 includes a shaft 14 which supports a patient interface balloon 16 at its distal end, an anti-migration disc 18, an introducer 20, and a handle 22 located at the proximal end of the shaft 14. An inflater cuff 24 is provided for supplying air to the patient interface balloon 16 and connects to the proximal end of the shaft by a tube 26. A stop cock 28 is provided in the tube 26 for controlling the passage of air through the tube 26 to the patient interface balloon 16.

As will be described in more detail hereinafter, a receiving coil is contained within the patient interface balloon 16 and electrically connected to the interface 12 by an insulated interconnecting cable 30 which has a plug 32 at its proximal end for connection to terminal 34 located on the front of the interface network 12.

The interface network 12 also includes a terminal 36 for providing a connection to a MRI scanner. Furthermore, the interface network 12 includes a switch 38 capable of being moved between an operating position and a tuning position. To display to the operator the mode of operation, indicator lights 40 are provided on the front of the interface network 12. In addition, a light 42 for indicating the occurrence of a probe failure is provided on the front of the interface network 12.

Referring now to FIGS. 2, 4, 5, and 8, the patient interface balloon 16 of the insertable pickup probe 10 is illustrated in more detail. The patient interface balloon 16 comprises an inner balloon 44 and an outer balloon 46. The inner balloon 44 is constructed of a flexible medical grade latex or other elastomeric material, which is preferably non-paramagnetic and has low dielectric losses, and is capable of being inflated with air supplied through a lumen 48 within the shaft 14, and expelled into the inner balloon 44 via a hole 49 in lumen 48. The inner balloon 44 is substantially cylindrical in shape except for an anterior substantially planar section which is covered with a non-stretchable substantially planar member 50, formed of, for example, an adhesive backed cloth material.

A receiving coil 52 is provided between the inner balloon 44 and the outer balloon 46 and is typically formed of a flexible conductive material. The receiving coil 52 is arranged between the non-stretchable member 50 and the outer balloon 46, is fed to the patient interface balloon 16 through a second lumen 54 in the shaft 14, and is fed out of the shaft 14 through a hole 56 in the shaft 14 inside the outer balloon 46.

The outer balloon 46 has a first wall position adjacent the region of interest, which can have an anterior saddle shape as indicated at reference number 62, for conformably fitting the rectal prostatic bulge inferior to the ampulla of the rectum. In addition, the outer balloon 46 has a second wall position generally comprised by posterior undulating folds 64 which allow the patient interface balloon 16 to unfold first when the inner balloon 44 is inflated. That is, the second position of the outer balloon moves preferentially with respect to the first position so that it can move into contact with a vessel wall generally opposite the region of interest during the initial stages of inflation of inner balloon 44. This unfolding forces the anterior surface 62 to hug the prostatic region of the rectum, thereby ensuring that the image field of view of the insertable pickup probe 10 will focus on the desired region of interest.

The non-stretchable member 50 serves two functions in the patient interface balloon 16. First, the member 50 controls the focus of the inflation stretch of the inner balloon 44; secondly, member 50 acts as a guide for the receiving coil 52. Upon inflation, the inner balloon 44 first stretches posteriorly away from the receiving coil 52. This initiates the folds 64 of the outer balloon 46 to force posteriorly against the rectum wall until the anatomy offers an equal resistance. Then, the non-stretchable member 50 rises and forces the receiving coil 52 and the anterior surface 62 of the outer balloon 46 against the region of interest. When inflation is complete, the receiving coil 52 is in position to receive the best possible RF signal from the region of interest.

Figure 4:
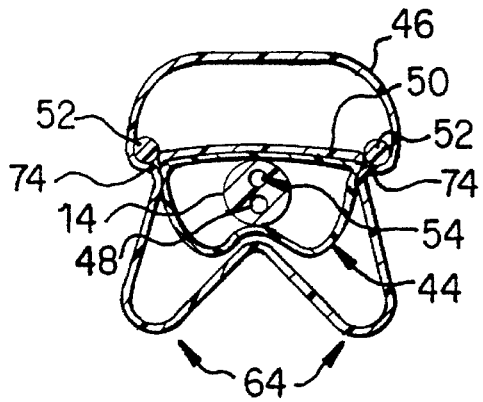
FIG. 4 is a sectional view taken through line 4—4 of FIG. 2.
Figure 5:
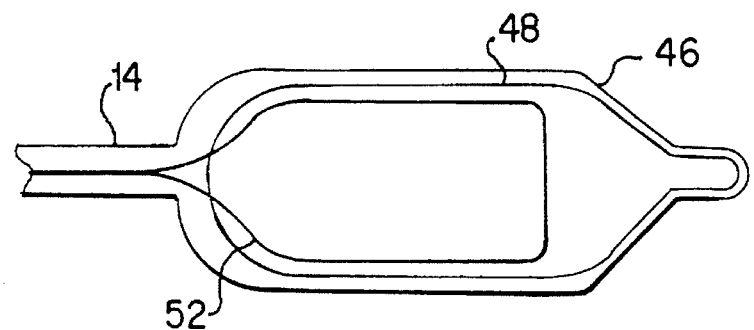
FIG. 5 is a top sectional view as seen from line 5—5 of FIG. 2.

In addition, as shown in FIG. 4, lateral indentations 74 are provided on the outer balloon 46 intermediate the first and second wall positions. The indentations 74 act as coil positioners when the balloon is in its uninflated state. The receiving coil 52 is positioned on the shelf formed by the indentations 74 during assembly of the probe. This allows the receiving coil 52 to be repeatedly positioned relative to the shelf inside the outer balloon 46 for numerous clinical inflation and deflation cycles.

Alternatively, the patient interface balloon 16 may be constructed with a single ply inflatable balloon of elastomeric material. In this arrangement, the receiving coil 52 would be bonded to the inside surface of the balloon.

Further yet, the interface balloon 16 may be constructed with a single multi-ply balloon. This balloon would have the receiving coil 52 encapsulated between the plies of the elastomeric material. When inflated, the receiving coil 52 would be forced against the region of interest by the movement of the balloon. The coil encapsulation would take place during the balloon fabrication process by placing the receiving coil 52 on the surface of the balloon and then redipping the balloon to place another ply of material over the outer surface of the balloon, thus covering the receiving coil 52.

To assist a clinician in the insertion of the pickup probe 10, a colored stripe 55 is painted or otherwise marked on the shaft 14. The stripe 55, best shown in FIG. 1, and also shown in FIG. 8, may include a scale for indicating the distance which the shaft 14 has been inserted into the-patient, and also the radial orientation of the balloon 16 for proper alignment with the prostate. In addition, the distal end 15 (hereinafter referred to as the flexible tip), of the shaft 14 which fits into the balloon 16 is typically more flexible than the remaining length of the shaft 14 to provide a more comfortable fit in the patient and to reduce the possibility of perforating tissue during use.

Figure 2:
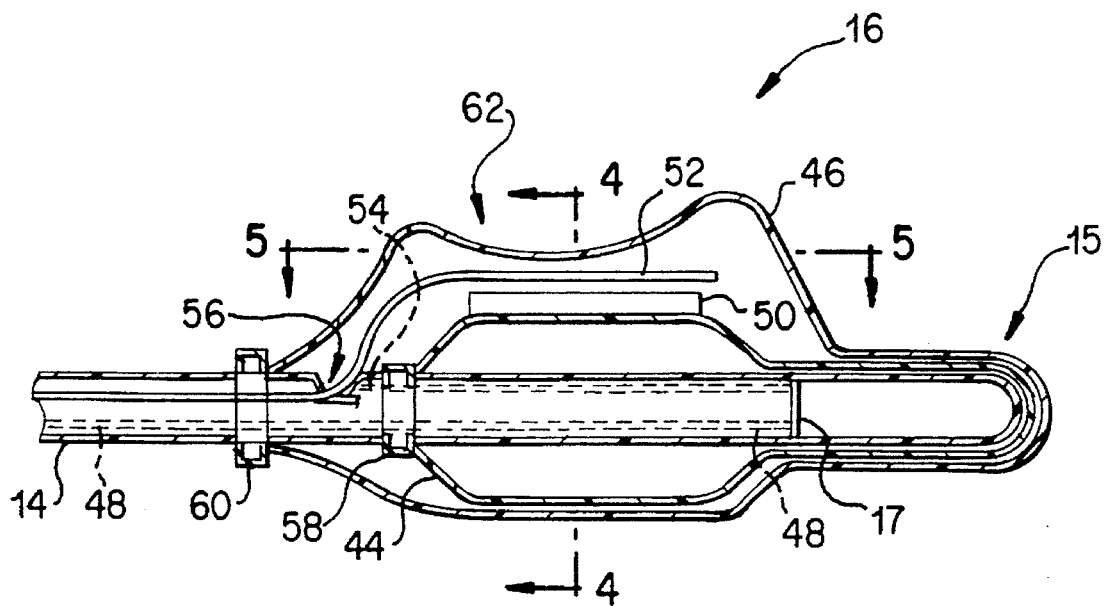
FIG. 2 is a cross-sectional view taken through line 2—2 of the distal inflatable balloon portion of the insertable pickup probe illustrated in FIG. 1.
Figure 8:
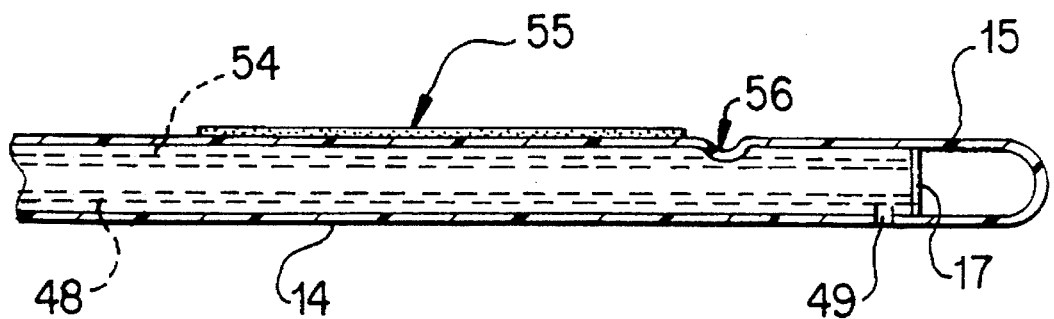
FIG. 8 is a cross-sectional view illustrating the shaft of the insertable pickup probe illustrated in FIG. 1.

Referring to FIGS. 1, 2 and 8, the shaft 14 is rigid so that when it is twisted radially at the handle 22, the balloon, shaft, and handle move as a unit to ensure alignment. The flexible tip 15 is typically made of a more flexible material than the shaft 14, and is bonded to the shaft 14 as indicated at reference numeral 17. The outer balloon 62 is anchored to the shaft 14 by a proximal clamp 60 and by an interference fit with the flexible tip 15 of the shaft 14. Similarly, the inner balloon 44 is anchored to the shaft 74 by a proximal clamp 58 and by an interference fit with the flexible tip 15. The outer balloon 46 completely encloses the flexible tip 15 of shaft 14 and inner balloon 44, as disclosed in FIG. 2.

Figure 3:
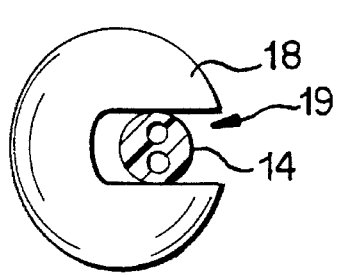
FIG. 3 is an end view as seen from line 3—3 of the insertable pickup probe illustrated in FIG. 1.

FIG. 3 illustrates the anti-migration disc 18 in more detail as it fits onto the shaft 14. The disc 18 is semi-spherical and constructed from semi-rigid plastic. The purpose of the anti-migration disc 18 is to prevent the pickup probe 10 from migrating superiorly due to the normal peristaltic activity of the colon. The disc 18 has a slot 19 which snaps onto the shaft, as shown in FIG. 3, adjacent the anal sphincter after the device has been operatively placed within the patient.

Figure 6:
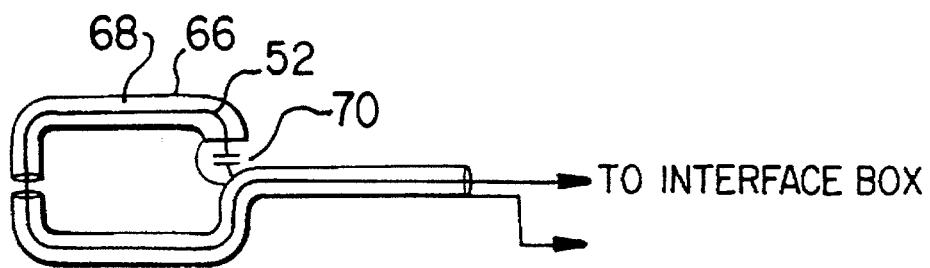
FIG. 6 is a schematic diagram illustrating the receiving coil and interconnecting cable of the insertable pickup probe of the present invention.
Figure 7:
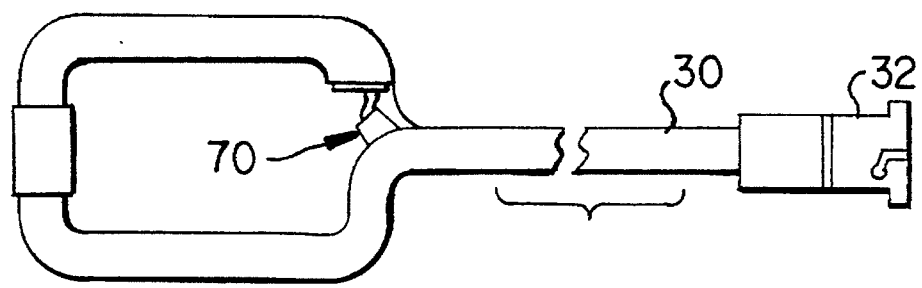
FIG. 7 is a schematic diagram illustrating the interconnecting cable and receiving coil fabricated from a single piece of coaxial RF cable in accordance with the present invention.

Turning now to FIGS. 6 and 7, the connection of the receiving coil 52 to the insulated interconnecting cable 30 will be described in more detail. The receiving coil 52 is a flexible single turn coil capable of picking up radio frequency (RF) signals. In the preferred embodiment, as mentioned previously, the inner balloon 44 of the patient interface balloon 16 displaces the receiving coil 52 to the inside of the anterior surface of the outer balloon 46 upon probe inflation. This optimizes the coupling between the coil 52 and the target anatomy. In order to minimize the dielectric losses in the probe-patient interaction, the receiving coil 52 is surrounded by a Faraday shield 66 to confine the majority of the coil electrostatic field within a coil-shield gap 68. Since the signal coupling from the NMR proton spin systems to the receiving coil 52 is achieved exclusively by magnetic means, the presence of the Faraday shield 66 will not detract from the NMR signal, as it is essentially transparent to magnetic field interaction.

The reduction of electrostatic field interaction between the patient and the probe will provide two benefits. First, there will be a reduced electrostatic loss, and thus a greater coil quality factor Q. Second, the effects of the specifics of a particular patient on coil tuning will be reduced due to the containment of the electrostatic field to a defined region. The use of the Faraday shielded coil design will also improve the signal-to-noise ratio performance of the coil 52 by raising the coil Q. In general, the signal to noise ratio of two geometrically equivalent coils is proportional to the square root of the loaded coil Q, as long as the apparent Q occurs only from the current flowing in the resonant path including the coil conductor.

The receiving coil 52 of the present invention, in its preferred form, is operated in a series resonant mode, and the interconnecting cable 30 is used as a resonant transformer to convert the probe impedance from a series resonance type to a parallel resonant one as seen at the plug 32 of the interconnecting cable 30. Typically, the interconnecting cable 30 is a coaxial cable. As illustrated in FIG. 7, the receiving coil 52 is resonated by a series capacitor 70. The length of the cable 30 is one quarter wavelength which allows remote tuning of the receiving coil with one half as much loss in the cable 30 in the series resonant configuration, rather than a parallel resonant configuration, which would employ a one half wavelength cable to connect the coil to the interface network 12. Use of the one quarter wavelength cable also simplifies the decoupling of the receiving coil 52, as will be described hereinafter.

As mentioned above, the connection of the pickup probe 10 to the interface network 12 is accomplished with a one quarter wavelength cable 30. In the preferred embodiment, the receiving coil 52 and the conductive portion of the cable 30 are fabricated from a single piece of coaxial RF cable as illustrated in FIG. 7. The interconnecting cable 30 serves two system functions. First, in the signal acquisition mode (receive mode), the cable transforms the series resonant coil to appear as a parallel resonant device, according to the well known relationship: $Z_{output} = (Z_{cable})(Z_{cable})/Z_{input}$ where $Z_{output}$ is the probe impedance as seen at the interface network 12, $Z_{cable}$ is the characteristic impedance of the cable 30 also used to construct the coil 52, and $Z_{input}$ is the series resonant impedance of the receiving coil 52 itself.

As will be described in more detail hereinafter, in the transmitting mode, when the coil 52 is to be decoupled, $Z_{output}$ is the resistance placed in series with the resonant path of the receiving coil 52 itself. $Z_{cable}$ is the characteristic impedance of the coaxial cable used to construct the receiving coil 52 and cable 30, and $Z_{input}$ is the RF resistance of the PIN diode or crossed diodes (illustrated in FIG. 9) when forward biased in the transmit mode.

In operation, the probe 10 is inserted intrarectally while the patient interface balloon 16 is in the uninflated relaxed state. The provided alignment guide 55 is used to radially and longitudinally position the probe 10 within or adjacent the region of interest. The patient interface balloon 16 is then inflated via the inflator cuff 24 to optimize the tissue to probe interface. The anti-migration disc 18 is then used to maintain proper positioning of the pickup probe 10 during the clinical scanning procedure. During insertion, the introducer 20 functions as a dilator for the anal sphincter. The funnel shaped introducer 20 slides easily over the entire length of the shaft 14. Without the introducer, the anal sphincter would contract around the shaft and interfere with the ability to radially and longitudinally position the pickup probe 10. Thus, the introducer 20 immediately follows the patient interface balloon 16 to prevent the anal sphincter from contracting around the shaft 14 of the pickup probe 10. The clinician can then have free movement of the probe 10 in the rectal cavity. Once the probe 10 is correctly placed, the introducer 20 is pulled inferiorly along the shaft 14, allowing the sphincter to contract around the shaft 14. This contraction assists in holding the probe 10 in place.

Once the patient interface balloon 16 is inflated, the stop cock 28 is moved to a closed position, thus allowing the clinician to disconnect the inflater cuff 24 without deflating the interface balloon 16. The probe 10 is then connected to the interface network 12 via plug 32 of the cable 30.

Figure 9:
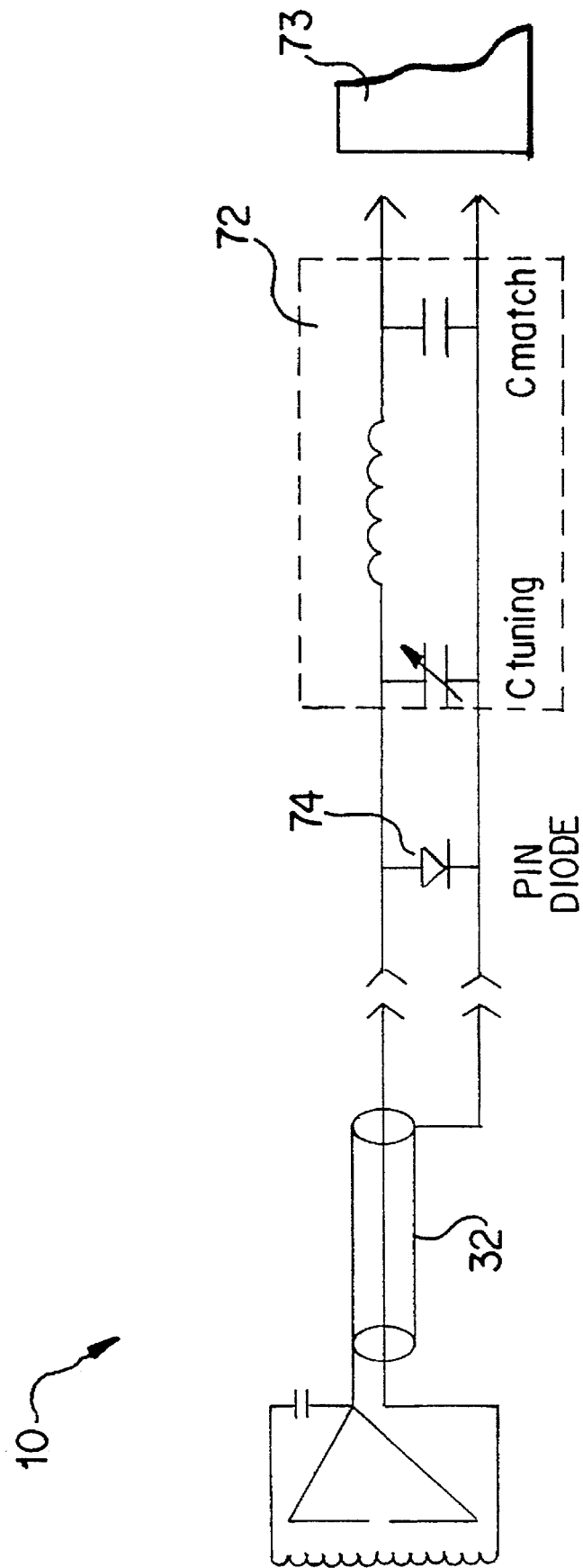
FIG. 9 is a schematic diagram illustrating the circuit for performing impedance matching of the probe illustrated in FIG. 1 with a remote MRI scanning system.
Figure 10:
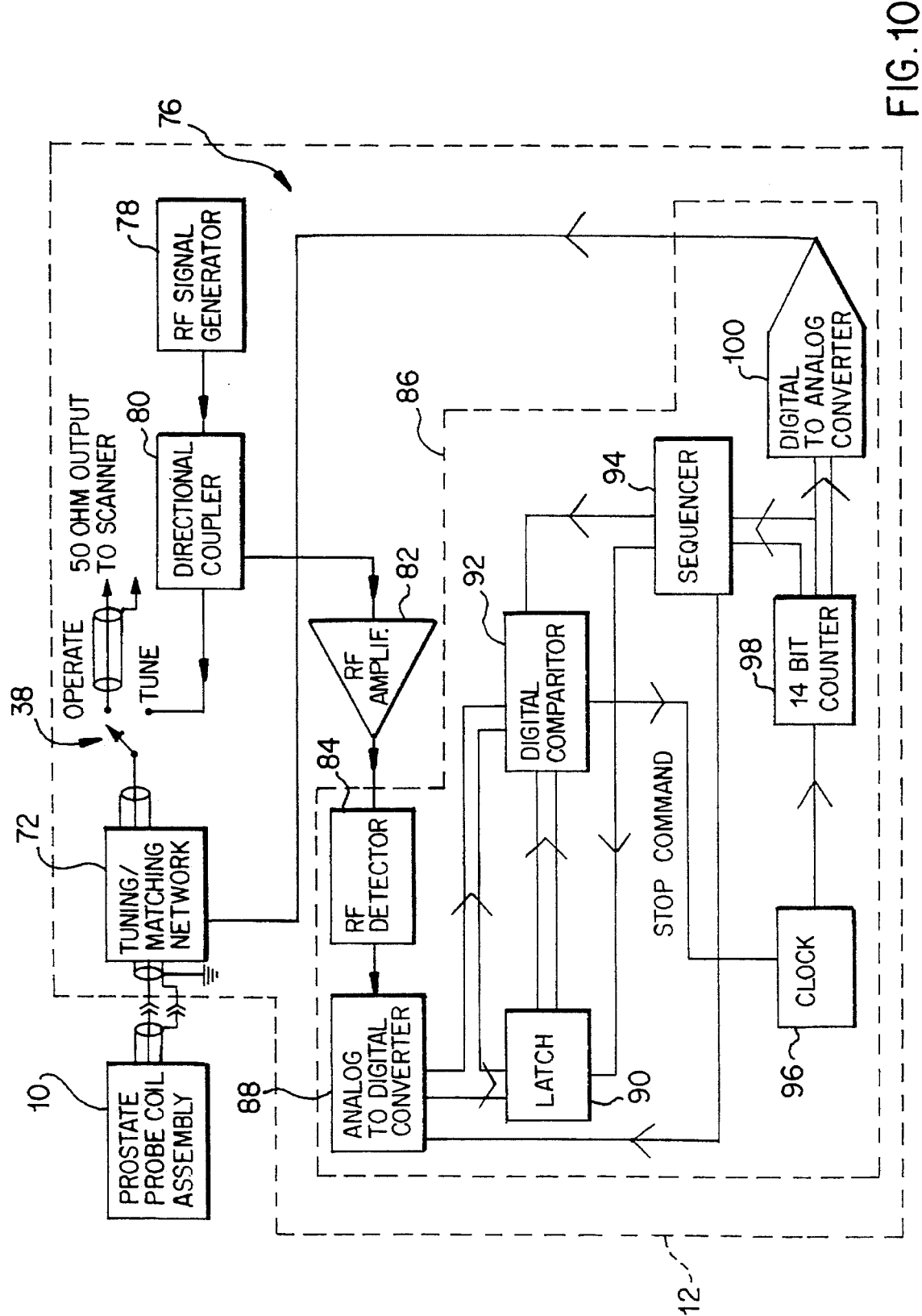
FIG. 10 is a schematic diagram illustrating the circuitry in the interface network for automatically tuning the receiving coil to a specific frequency for a remote MRI scanner.
Figure 11:
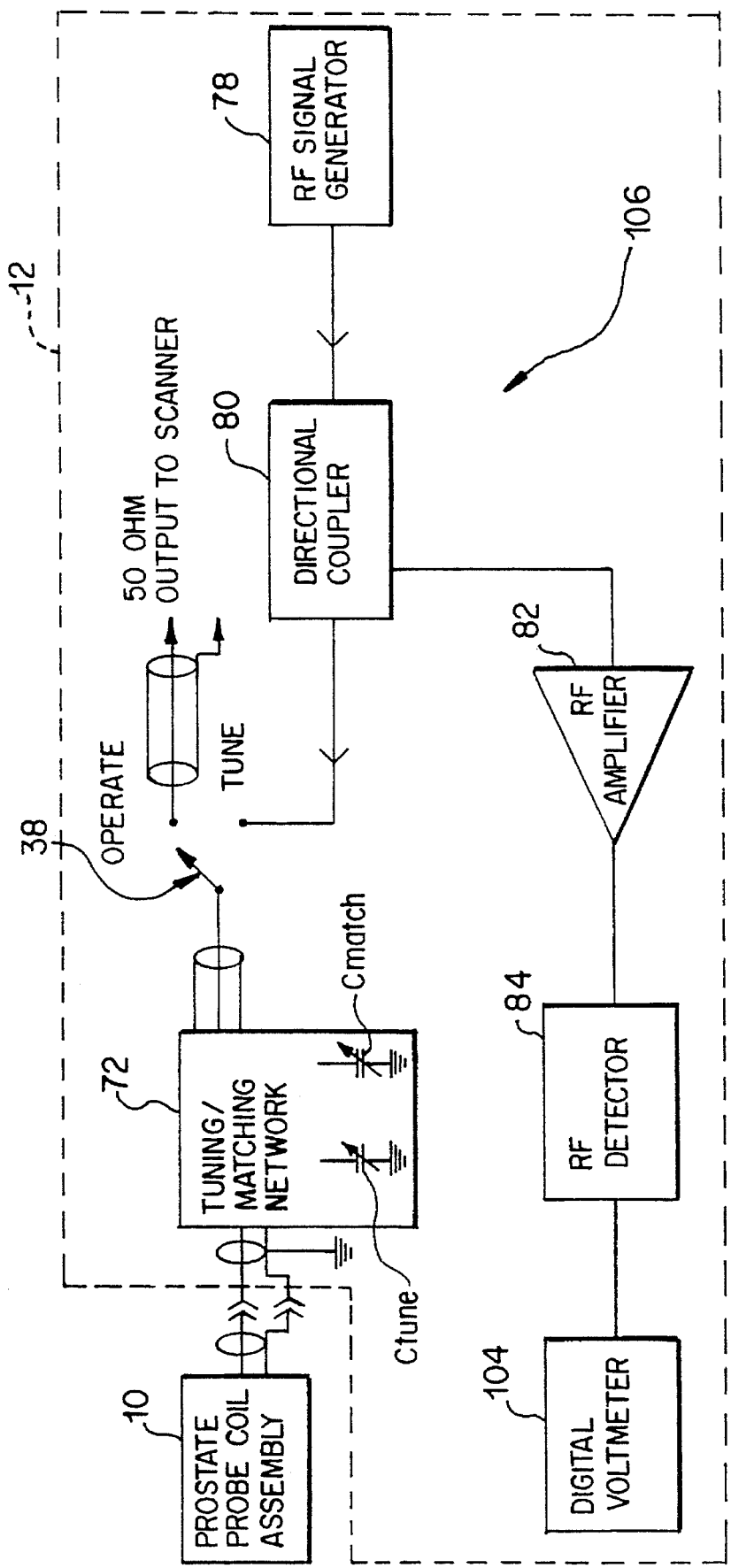
FIG. 11 is a schematic diagram illustrating the circuitry of the interface network for manually or automatically tuning and impedance matching the receiving coil to a remote MRI scanner.

Referring now to FIGS. 9–11, the interface network 12 will be described in detail as it is used with the insertable pickup probe 10 and a MRI or NMR scanner 73. The interface network 10 serves three purposes: tuning of the receiving coil 52 of the probe 10 to the Larmour frequency of the MRI or NMR scanner 73; transforming of the output impedance of the probe 10 to match the scanner input impedance, which is typically 50 ohms; and, decoupling of the probe 10 during the transmit portion of the scanning sequence. Tuning may be accomplished manually or automatically. In the preferred embodiment, an electronic optimization circuit is provided to automatically adjust the resonance of the probe 10.

The receiving coil 52 of the probe 10 is series resonant and includes a transformer in the form of the one quarter wavelength cable 30 to convert the series resonance to a parallel resonance. The frequency of resonance may be altered by placing an appropriate reactance between the scanner 73 and the interconnecting cable 30, remote from the probe 10 itself. As such, the probe 10 may be tuned to the scanner 73 after the probe is inserted into the patient.

As shown in FIG. 9, the interface 12 includes a conventional Pi network 72 consisting of a single series inductor L, and shunting capacitors $C_{tune}$ and $C_{match}$, at each end of the network 72. To facilitate tuning of the probe 10, the input capacitor $C_{tune}$ of the Pi network 72 is made variable as illustrated. Thus, by changing the value of this capacitor, either manually, or automatically by electronically changing the voltage across a varactor diode which may be substituted for the capacitor $C_{tune}$, the net reactance appearing across the output of the cable 30 from the probe 10 is adjusted. Since some of the reactance of the capacitor $C_{tune}$ is absorbed into the Pi network 72, the apparent reactance presented to the probe output can appear resistive, capacitively reactive, or inductively reactive. This allows the probe to be tuned both above and below its natural resonant frequency, while limiting the level of circulating resonance current in the interconnecting cable 30 to the lowest possible value (ideally zero in the case where the natural resonance of the insertable pickup probe matches the Larmour frequency of the MRI or NMR scanner).

For automatic tuning of the probe 10, the control voltage for the varactor diode substituted for the capacitor $C_{tune}$ in the Pi network 72, is obtained from an electronic tuning circuit described hereinafter. Under manual tuning, the operator simply adjusts the variable capacitor $C_{tune}$ to reduce the S11 parameter of the receiving coil 52 as seen at the output port 36 of the interface network 12, to the minimum value. As is well known in the art, the S11 parameter is the scattering parameter of standard RF measurements which indicates the ratio of reflected to incident power at the input port of a network. When the reflected power is 0, representing a voltage standing wave ratio (VSWR) of 1.0:1, the S11 parameter is also 0. When the VSWR is infinite, representing all the incident power being reflected at the input port, the S11 parameter is 1.0.

To match the impedance of the probe 10 to the scanner 73, transformation of the real part of the output impedance (in the range of 1,000 to 1,500 ohms in the preferred embodiment at 64 MHz) of the probe 10 is accomplished with the Pi network 72 of FIG. 9. Any impedance matching network design could be used in place of the Pi network 72 illustrated in FIG. 9. The values of the various components comprising the Pi network 72 are chosen to match the impedances of the probe 10 and scanner 73.

During the transmitting portion of the scanning procedure, the probe 10 must be decoupled from the MRI scanner 73 to prevent distortion of the transmitted magnetic field. This is accomplished by the use of an RF switch at the probe input terminal 34 of the interface network 12. A PIN diode 74 or crossed RF switching diodes can be used at this location, as illustrated in FIG. 9, to create a very low impedance at the resonant frequency of the probe 10 during transmit excitation. Because of the impedance transforming capability provided by the one quarter wavelength cable 32, the PIN diode 74 is forward biased with exceptionally low RF resistance to appear as an open circuit in series with the receiving coil 52. This limits the RF current flow within the receiving coil 52 to a very low value, and effectively decouples the receiving coil 52 from the incident RF magnetic excitation field transmitted into the patient. This arrangement allows the decoupling diode switch 74 to be located remote from the probe 10, and can be reused as part of the interface network 12 after the probe 10 is disposed.

Referring now to FIG. 10, the circuitry for accomplishing the automatic tuning of the receiving coil 52 of the probe 10 is generally shown at 76. This circuitry is incorporated within the interface network 12 and operates by sampling the S11 parameter of the probe 10 and Pi network 72, to generate a control voltage for tuning the probe 10 with the varactor diode, substituted for $C_{tune}$, at the probe input terminal 34 of the interface network 12, and a circuit to lock the control voltage at the value which optimizes the S11 parameter. The value of the S11 parameter is determined by using a local signal source 78 to replace the scanner output terminal 36 on the interface network 12 during the tuning procedure as accomplished by the switch 38 of the interface network 12. A directional coupler 80, connected to the local signal source 78 obtains a sample of the reflected power from the signal source when using the probe 10 and the interface network 12 as a load. This sample is fed to an amplifier 82 and converted to a DC level. The resulting DC signal is then fed into a slope detector 86 of either analog or digital design.

The slope detector 86, for example, may comprise a RF detector 84 and an analog to digital converter 88 connected to a latch circuit 90 and a digital comparator 92. The analog to digital converter 88 is also connected, together with the latch circuit 90 and the digital comparator 92 to a sequencer 94. The digital comparator 92 provides an output stop command signal to a clock circuit 96 which controls the contents of a counter 98. The value within the counter 98 determines the value of the control voltage to be applied to the varactor diode which is converted from a digital signal to an analog signal by the digital to analog converter 100.

In general terms, the slope detector 86 determines the minimum point of a function, which function in this case is the ratio of reflected to incident power (the S11 parameter). This function monotonically increases in both directions from the minimum point. As the tuning is swept, the function is dropped until a minimum is reached, and then begins to increase again.

The digital slope detector 86 compares the digitized voltage level of a present data point of the function, with the previous data point. When it is found that the present data point is equal to or greater than the previous point, a level shift from logic 0 to logic 1 is output. The control voltage produced at the output of the digital to analog converter 100 is ramped from a minimum value towards a maximum value. When the DC level representing the S11 parameter reaches zero slope as it drops from a starting value, the varactor control voltage is locked to the value at that point.

Alternatively, the slope detector may be of an analog design comprising an operational amplifier-differentiator circuit. This circuit takes the first derivative of the voltage level. As the first derivative or slope reverses direction, the operational amplifier output ramps rapidly from its negative rail voltage towards its positive rail voltage. This occurrence can be used as a stop pulse to indicate the minimum.

The slope detector circuit 86 can also be used to indicate probe failure. This is accomplished in two ways. First, the tuning of the S11 function never crosses a minimum, or secondly, if the absolute value of the tuning function (S11) becomes greater than a predetermined maximum acceptable value at the minimum. The first condition is an indication of a non-resonant probe, either due to component tolerance, failure, or improper construction. The second condition reveals a probe with an excessively low or high Q, typically indicative of improper construction or faulty materials.

Manual tuning can be accomplished by the circuit illustrated in FIG. 11 and generally shown at 106. All of the elements of circuit 106 are similar to that of circuit 76 with the exception of the digital voltmeter 104 substituted for the slope detector circuit 86. The reflected power during the tuning procedure is displayed as a scaler quantity on the digital voltmeter 104 to provide information to the operator relating to the status of the probe tuning. The capacitance of the capacitor $C_{tune}$ is manually varied during this procedure to minimize the reflected power.

Alternatively, in the event that the probe system requires the ability to automatically control the impedance matching as well as tuning, a second varactor illustrated as $C_{match}$ in FIG. 11, may be employed as the output capacitor of the Pi network 72. Adjustment of this reactance in an iterative fashion together with the adjustment of the tuning capacitor $C_{tune}$ may be accomplished by the automatic tuning circuit illustrated in FIG. 10 by toggling the optimization function between the two capacitors.

The interface network 12 enjoys the benefits of placing all of the decoupling, tuning, and impedance matching hardware remote from the probe 10 itself to make the probe 10 compatible with MRI and NMR scanners of different designs by modifying only the interface network 12 and not the probe 10. Thus, all systems operating at any specific frequency, such as the various 1.5 Tesla systems, could be accommodated by a single probe type; the variations in the system interface requirements such as the decoupling method (active or passive), connector type, input impedance, and the like could be accommodated by system-specific interface designs. In addition, the interface network 12 can be designed to be applicable to a family of probes of similar designs.

The above description is intended by way of example only and is not intended to limit the present invention in any way except as set forth in the following claims.

We claim:

1. An insertable intracavity probe for use in a magnetic resonance system for obtaining images or spectra of a region of interest within a cavity of a patient, the probe comprising:

a flexible support member having a distal tip and a shaft, said tip being substantially more flexible than said shaft;

an inflatable inner balloon connected to the flexible support member;

a flexible outer balloon completely enclosing said distal tip of the flexible support member and the inner balloon and for use in positioning the inner balloon within the cavity of the patient; and means for receiving RF signals from the region of interest substantially contained between the inner balloon and the outer balloon.

2. The probe of claim 1 further comprising a surface on the outer balloon having an anterior saddle shape for conformably fitting to the rectal prostatic bulge of the patient.

3. The probe of claim 2 further comprising folds on a further surface of the outer balloon opposite to the surface having the anterior saddle shape.

4. The probe of claim 3 further comprising a means for control of the inflation of the inner balloon and for positioning the means for receiving RF signals for optimal reception of the RF signals from the region of interest.

5. The probe of claim 4 wherein the means for control is a non-stretchable substantially planar member covering a surface on the inner balloon.

6. The probe of claim 2 further comprising inflating means connected to the flexible support member for inflating the inflatable inner balloon.

7. The probe of claim 6, wherein the inflating means comprises a compressible inflator cuff and a tube connected to the flexible support member to deliver air upon compression of the cuff to the inner balloon.

8. The probe of claim 1, wherein the flexible support member includes a positioning scale printed on the outer surface thereof.

9. The probe of claim 1, wherein the inner balloon and the outer balloon comprise a non-paramagnetic, flame retardant, biocompatible medical grade material having low dielectric loss characteristics.

10. The probe of claim 1, further comprising an anti-migration means for preventing unwanted movement of the probe relative to the cavity of the patient.

11. The probe of claim 10, wherein the anti-migration means is a disc having a semi-spherical shape and a slot which snaps into the flexible support member.

12. The probe of claim 1, further comprising a dilator element slidably mounted on the flexible support member for dilating an orifice leading to the cavity to allow easy positioning of the probe within the cavity.

13. The probe of claim 1, wherein the outer balloon further comprises lateral indentations for positioning the means for receiving RF signals on the indentations when the outer balloon is uninflated.

14. The probe of claim 1, wherein the means for receiving RF signals is a flexible coil.

15. The probe of claim 1 further comprising relay means electrically coupled to the means for receiving RF signals for providing an electrical output signal from the probe.

16. The probe of claim 15 further comprising first and second lumens contained within the flexible support member, the inflating means being connected to the inflatable inner balloon via the first lumen, and the relay means being an interconnecting cable for providing electrical connection to the means for receiving RF signals via the second lumen of the flexible support member.

17. An insertable intracavity probe for use in a magnetic resonance system for obtaining images or spectra of a region of interest within a cavity of a patient, the probe comprising:

a flexible support member;

an inflatable balloon connected to the flexible support member and having an anterior saddle shaped surface for conformably fitting to the rectal prostatic bulge of the patient; and a flexible coil adjacent to said inflatable balloon for receiving an RF signal from the region of interest.

18. The probe of claim 17, wherein the inflatable balloon comprises an inflatable inner balloon connected to the flexible support member, a flexible outer balloon enclosing the inner balloon and flexible coil for use in positioning the probe within the cavity of the patient.

19. The probe of claim 17, further comprising folds on a further surface of the balloon opposite to the anterior saddle shaped surface.

20. An insertable intracavity probe for use in a magnetic resonance system for obtaining images of a region of interest within a cavity of a patient, the probe comprising:

a flexible support member;

an inflatable planar balloon connected to the flexible support member and having undulating folds; and a flexible coil attached to the interior perimeter of the balloon;

such that when the balloon is inflated, the undulating folds press against a wall of the cavity generally opposite the region of interest to secure the balloon adjacent the region of interest.

21. The probe of claim 20 further comprising inflating means connected to the flexible support member for inflating the inflatable balloon.

22. The probe of claim 20, wherein the balloon comprises a non-paramagnetic, flame retardant, biocompatible medical grade material having low dielectric loss characteristics.

23. The probe of claim 20, wherein the inflatable balloon comprises an inflatable inner balloon connected to the flexible support member, and a flexible outer balloon enclosing the inner balloon and flexible coil for use in positioning the probe within the cavity of the patient.

24. The probe of claim 20 in combination with a magnetic resonance system, the system comprising:

a magnetic resonance imaging scanner; and a separable interface network for coupling said probe with said scanner and including impedance matching means to match the output impedance of said probe with the input impedance of the scanner, tuning means to tune the resonant frequency of the probe to the Larmour frequency of the scanner, decoupling means for decoupling the probe from the scanner during a magnetic resonance imaging transmission procedure.

25. The probe of claim 20 further comprising relay means electrically coupled to the flexible coil for providing an electrical output signal from the probe.

26. A method for obtaining magnetic resonance information from a region of interest within a cavity of a patient, the method comprising the steps of:

(a) providing an insertable probe comprising a flexible support member, an inflatable planar balloon connected to the flexible support member and having posterior undulating folds, and a flexible RF receiving coil attached to the interior perimeter of the balloon;

(b) inserting the insertable probe into a position in the cavity of the patient adjacent the region of interest;

(c) inflating the insertable probe, thereby unfolding the undulating folds against a wall of the cavity generally opposite the region of interest, and securely positioning the flexible RF receiving coil proximate the region of interest;

(d) inducing RF signals in the region of interest;

(e) sensing RF signals with the RF receiving coil;

(f) producing a magnetic resonance image by processing the received RF signals.

27. The method of claim 26 further comprising the steps of:

impedance matching the output impedance of the received RF signals with an input impedance of a scanner;

tuning the resonant frequency of the RF receiving coil to the Larmour frequency of the scanner;

decoupling the RF receiving coil from the scanner when inducing RF signals in the region of interest to prevent distortion of the received RF signals.

28. A magnetic resonance imaging system comprising:

an intracavity probe insertable within a cavity of a patient proximate a region of interest, the probe comprising a flexible support member having a distal tip and a shaft, said tip being substantially more flexible than said shaft; an inflatable inner balloon connected to the flexible support member; a flexible outer balloon completely enclosing said distal tip of the flexible support member and the inner balloon and for use in positioning the inner balloon within the cavity of the patient; and means for receiving RF signals from the region of interest substantially contained between the inner balloon and the outer balloon;

a magnetic resonance imaging scanner for producing data corresponding to an MRI image of the region of interest from the RF signals received by said RF receiving means; and an interface means electrically connected to said scanner for electrically connecting the RF receiving means to the scanner, the interface means including an impedance matching means for matching an output impedance of the RF receiving means with an input impedance of the scanner, and a tuning means for tuning the resonant frequency of the RF receiving means to the Larmour frequency of the scanner.

29. The system of claim 28, wherein the interface means comprises a decoupling means for decoupling the RF receiving means from the scanner to prevent distortion of the received RF signals.

* * * * *